United States Patent
Lenna et al.

(10) Patent No.: US 9,695,213 B2
(45) Date of Patent: Jul. 4, 2017

(54) PROCESS FOR THE PREPARATION OF DROSPIRENONE

(71) Applicant: Industriale Chimica S.r.l., Milan (IT)

(72) Inventors: Roberto Lenna, S. Giorgio Su Legnano (IT); Johannes Bernardus Maria Rewinkel, Berghem (NL); Francesco Barbieri, Bovision Masciago (IT); Maria Giovanna Luoni, Cardano Al Campo (IT)

(73) Assignee: INDUSTRIALE CHIMICA S.R.L. (IT)

( * ) Notice: Subject to any disclaimer, the term of this patent is extended or adjusted under 35 U.S.C. 154(b) by 7 days.

(21) Appl. No.: 14/768,659

(22) PCT Filed: Feb. 20, 2013

(86) PCT No.: PCT/IB2013/051377
§ 371 (c)(1),
(2) Date: Aug. 18, 2015

(87) PCT Pub. No.: WO2014/128525
PCT Pub. Date: Aug. 28, 2014

(65) Prior Publication Data
US 2016/0002284 A1 Jan. 7, 2016

(51) Int. Cl.
C07D 307/94 (2006.01)
C07J 53/00 (2006.01)

(52) U.S. Cl.
CPC ........... *C07J 53/008* (2013.01); *C07J 53/004* (2013.01)

(58) Field of Classification Search
CPC .................................................. C07D 307/94
USPC ........................................................ 549/456
See application file for complete search history.

(56) References Cited

U.S. PATENT DOCUMENTS

2012/0220792 A1    8/2012    Ma et al.

FOREIGN PATENT DOCUMENTS

| EP | 0075189 B1 | 8/1985 |
| EP | 0981791 B8 | 4/2001 |
| EP | 1828222 B1 | 12/2010 |
| EP | 2551275 A1 | 1/2013 |
| WO | 2006/061309 A1 | 6/2006 |

OTHER PUBLICATIONS

Ma, S. et al., "Development of a General and Practical Iron Nitrate/TEMPO-Catalyzed Aerobic Oxidation of Alcohols to Aldehydes/Ketones: Catalysis with Table Salt", Advanced Synthesis & Catalysis, 2011, pp. 1005-1017, vol. 353.

*Primary Examiner* — Douglas M Willis
(74) *Attorney, Agent, or Firm* — Fish & Tsang, LLP

(57) ABSTRACT

A process is described wherein, by employing 17α-(3-hydroxypropyl)-6β,7β;15β,16β-dimethylene-5β-androstane-3β,5,17β-triol (II) as starting product, in a single stage reaction there is obtained drospirenone, (I), a synthetic steroid with progestogenic, antimineralocorticoid and antiandrogenic action, that is useful for preparing pharmaceutical compositions with contraceptive action.

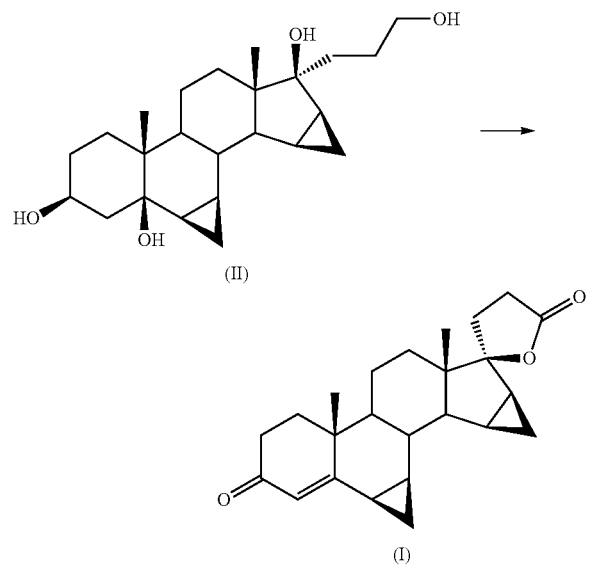

5 Claims, No Drawings

PROCESS FOR THE PREPARATION OF DROSPIRENONE

FIELD OF THE INVENTION

The present invention relates to the field of processes for the synthesis of steroids, and in particular to a process for the preparation of drospirenone on an industrial scale.

BACKGROUND

The compound of formula (I) below, the chemical name of which is 6β,7β;15β,16β-dimethylene -3-oxo-17α-pregn-4-ene-21,17-carbolactone, is commonly indicated by the name drospirenone:

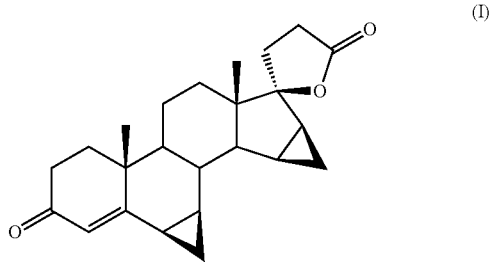 [SMILES: C[C@]12CCC(=O)C=C1[C@@H]1C[C@@H]1C1C2CC[C@@]2(C)C1[C@@H]1C[C@@H]1[C@@]21CCC(=O)O1]

(I)

Drospirenone is a synthetic steroid with progestogenic, antimineralocorticoid and antiandrogenic action; thanks to these characteristics, it has been used for some time in the preparation of pharmaceutical compositions with contraceptive action for oral administration.

Various processes for the preparation of drospirenone are known in literature.

The process described in European patent EP 075189 B1 obtains the end product drospirenone by hot oxidation of 17α-(3-hydroxypropyl)-6β,7β;15β,16β-dimethylene -5β-androstane-3β,5,17β-triol with the mixture pyridine/water/chromic anhydride. This step constitutes a substantial drawback of the process: indeed, chromic anhydride, like all Cr(VI) compounds, is a proven carcinogen, the use of which is subject to legislative restrictions such that the precautions required during its use and disposal make it virtually unusable.

Another process for the preparation of drospirenone is described in European patent EP 918791 B8; in the process of this document the drospirenone is obtained, again starting from 17α-(3-hydroxypropyl)-6β,7β;15β,16β-dimethylene-5β-androstane -3β,5,17β-triol, in two distinct phases and employing an oxidant such as for example potassium bromate in the presence of ruthenium salts as catalysts, which necessarily must then be completely eliminated from the product.

European patent EP 1828222 B1 describes a further process, wherein the oxidation step is accomplished by using calcium hypochlorite as oxidant in the presence of 2,2,6,6-tetramethylpiperidine-1-oxyl radical or a derivative thereof as a catalyst; in the process of this patent the oxidant is added in portions until completion of the reaction. This process overcomes the disadvantages of the prior art since the calcium hypochlorite is not a carcinogenic reagent, nor is 2,2,6,6-tetramethylpiperidine-1-oxyl radical a metal catalyst that imposes a purification of the end product; however, the need for subsequent additions of reagent and the analytical controls in the course of reaction, however simple, are a hindrance to a standardized production that must proceed continuously or nearly so. Consequently, the method of this patent too has process drawbacks from the point of view of an industrial production.

There is therefore still a need to have a simple process that allows the drawbacks of the prior art to be overcome.

SUMMARY OF THE INVENTION

The object of the present invention is thus to provide an industrial process that allows the preparation of drospirenone while avoiding the use of reagents that are hazardous or the use of which is in any case restricted by industry regulations, and minimizing operator interventions during the process itself.

This object is achieved with the present invention, which relates to a process for the production of drospirenone comprising the reaction of the compound 17α-(3-hydroxypropyl) -6β,7β;15β,16β-dimethylene-5β-androstane-3β,5,17β-triol with gaseous oxygen in the presence of catalytic amounts of 2,2,6,6-tetramethylpiperidine -1-oxyl radical (or a derivative thereof), a ferric salt and sodium chloride, in a solvent consisting of acetic acid or a mixture of an acid and at least one organic solvent, at a temperature of between 30 and 50° C.

The definition "catalytic amounts" means a molar non-stoichiometric amount of reagent, i.e. below the theoretical stoichiometric amount needed if the compound were the primary oxidant of the reaction.

In the reaction, the compound 17α-(3-hydroxypropyl)-6β,7β;15β,16β-dimethylene-5β-androstane -3β,5,17β-triol, having the formula (II) below, can be in a mixture with one or both its lactols, as described in example 6 of the cited patent EP 1828222 B1. The reaction scheme (reaction scheme 1) is as follows, wherein the lactols are shown in parentheses to indicate that they may or may not be present, and the symbol ⁓ in the lactols formula indicates that the —OH group can be located either above or below the plane of the molecule (thus, respectively, in β or α configuration):

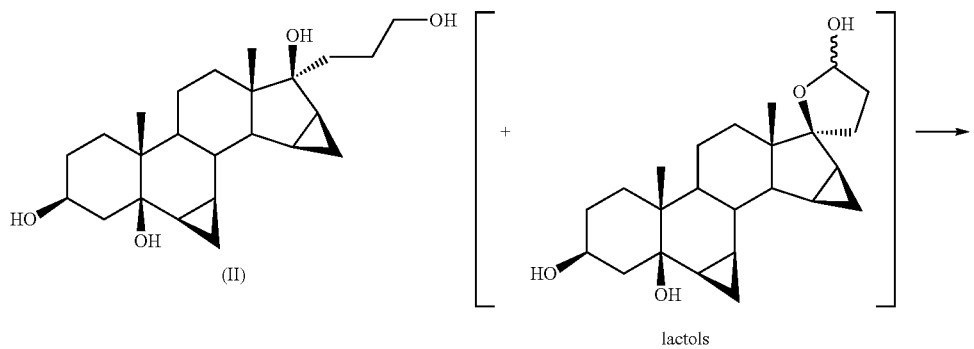

lactols

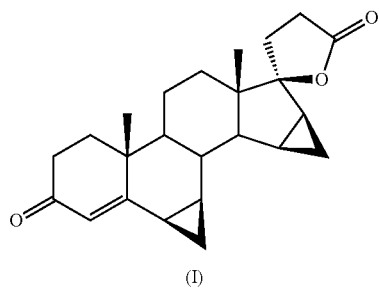

(I)

The solvent consists of pure acetic acid, or of acetic acid or another acid in a mixture with one or more organic solvents.

Said reaction allows drospirenone to be obtained directly, in a single process step, thus eliminating the need for subsequent additions of other reagents such as for example a protic acid or a base in intermediate reaction steps to complete the conversion.

Characteristics and advantages of the present process are illustrated in detail in the following description.

DETAILED DESCRIPTION

The Applicant has developed a new, extremely simple process, which allows drospirenone to be obtained using oxygen in the presence of a catalytic system consisting of 2,2,6,6-tetramethylpiperidine-1-oxyl radical or a derivative thereof, a ferric salt (i.e. in which iron is in the oxidation state (III)) and sodium chloride, and in a solvent consisting of, or comprising, an acid.

The compound 2,2,6,6-tetramethylpiperidine-1-oxyl radical is known in the field with the abbreviation TEMPO, which will be used hereinafter The oxidation of alcohols with TEMPO, ferric nitrate and sodium chloride was recently described in the article "Development of a general and practical iron nitrate/TEMPO- -catalysed aerobic oxidation of alcohols to aldehydes/ketones: catalysis with table salt" published in Adv. Synth. Catal. 2011, 353, 1005-1017.

From reading this article, however, an expert in steroid chemistry would not have been directed to apply what is described in the reaction of the present invention.

In the article abstract, the authors clearly state that the oxidations of simple alcohols (alkyl- and phenyl-carbinols and allyl alcohols) with oxygen are well known while the object of the article is to provide an oxidation method for allenols and propargyl alcohols.

No reference is made to complex molecules such as steroids or to the possibility of obtaining transformations other than an oxidation from alcohol into aldehyde or ketone.

The described oxidation, in 1,2-dichloroethane as preferred solvent, serves for selectively obtaining ketones and/or aldehydes from alcohols. No example is described for the obtaining of an acid from an alcohol or of a lactone from a lactol, transformations which on the other hand are necessary for obtaining drospirenone. 1,2-dichloroethane, used at room temperature, is the preferred solvent indicated in the article, as clearly stated on page 1011, paragraph "Typical procedures for the synthesis of aldehydes or ketones" of the article.

From reading the article, a person skilled in the art would not have learned the indication of using an acid as reaction solvent, alone or in combination with an organic solvent, at a temperature of between 30 and 50° C.

The reactions involved in the transformation from (II) (and possibly lactols) into (I) of scheme 1 are manifold and comprise the formation of a double bond by elimination of water and the ex-novo formation of a lactone ring; in particular, oxidation, cyclization and dehydration reactions are necessary in said transformation; these reactions are illustrated in the diagram below, in the top two lines of which there are indicated the transformations taking place at the carbon in position 17 of the steroid skeleton (in case the reagent is a lactol, the transformation consists only of the last step indicated in the top line), while in the bottom line there are indicated the transformations taking place at the ring A (as per IUPAC nomenclature) of the steroid skeleton:

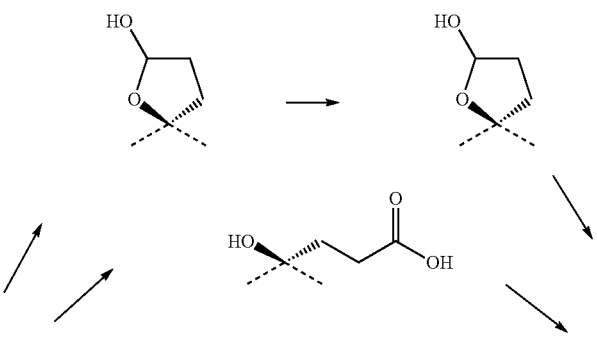

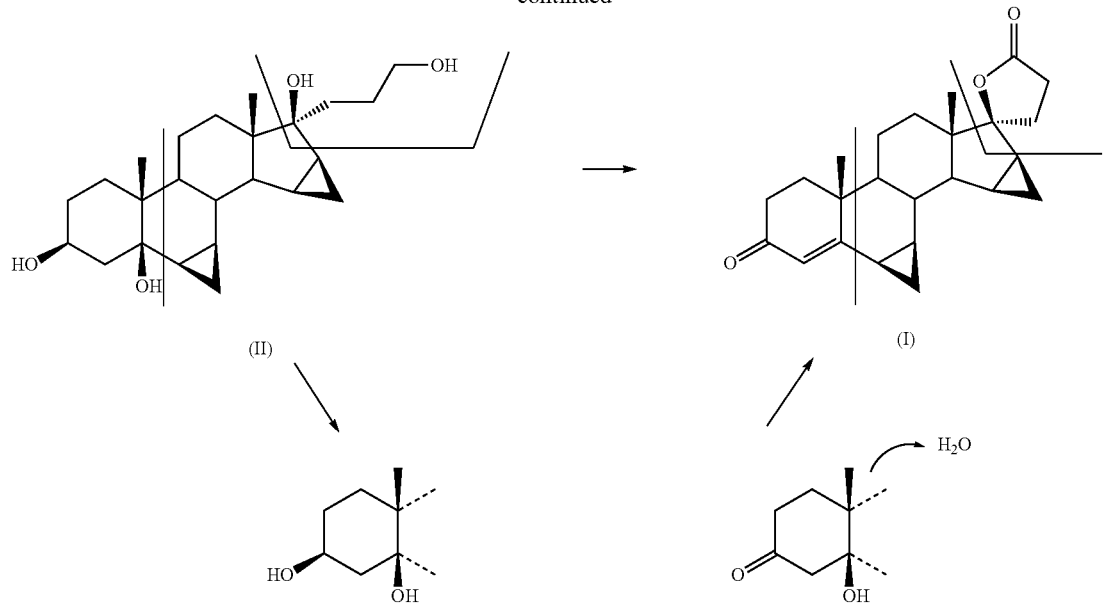

In contrast to what is described in European patent EP 1828222 B1 and in EP 918791 B8, in the present invention all the reagents are loaded into the reaction vessel in a single addition, without the need for further interventions in the course of the reaction, and all the above-indicated reactions occur in the course of a single process step.

The oxidation substrate of the present process, i.e. 17α-(3-hydroxypropyl) -6β,7β;15β,16β-dimethylene-5β-androstane-3β,5,17β-triol (or a mixture thereof with the corresponding lactols) can be obtained starting from commercial products by means of procedures known to a person skilled in the art. Preferably, said compound is obtained according to the procedure described in steps a) to f) of patent EP 1828222 B1.

Gaseous oxygen can be supplied into the reaction vessel as pure oxygen, air, or a synthetic mixture of oxygen with an inert gas (for example, the so-called synthetic air, widely used in the medical field); oxygen, in any one of these forms, can be used in static conditions, i.e. in a closed vessel containing a gaseous atmosphere consisting of or containing oxygen, or in conditions of slight flow of the same gaseous atmosphere.

As mentioned, as first component of the catalytic system it is possible to use the compound known as TEMPO or derivatives thereof; the TEMPO derivatives of possible use are 4-hydroxy-2,2,6,6-tetramethylpiperidine-1-oxyl radical, 4-methoxy -2,2,6,6-tetramethylpiperidine-1-oxyl radical, 4-(benzoyloxy)-2,2,6,6-tetramethylpiperidine-1-oxyl radical, 4-acetamido-2,2,6,6-tetramethylpiperidine-1-oxyl radical and 4-amino-2,2,6,6-tetramethylpiperidine-1-oxyl radical. This component is used in an amount of between 15 and 25% in moles, preferably 20% in moles, with respect to the reaction substrate.

The TEMPO catalyst or the derivatives thereof are added in a single portion at the start of the reaction and are not affected by the acid reaction environment.

The second component of the catalytic system is a ferric salt such as, for example, ferric nitrate nonahydrate $Fe(NO_3)_3 \cdot 9H_2O$, which is added as fine powder in an amount of between 15 and 25% in moles, preferably 20% in moles, with respect to the reaction substrate.

The third component of the catalytic system is sodium chloride, which is added as fine powder in an amount of between 15 and 25% in moles, preferably 20% in moles, with respect to the substrate to be oxidized.

Acetic acid can be used as solvent for the reaction, either alone or in a mixture with an organic solvent; the solvent must clearly be inert under the reaction conditions, and can be selected from ethyl ether, diisopropyl ether, methyl t-butyl ether, tetrahydrofuran, methyltetrahydrofuran, ethyl acetate, isopropyl acetate, butyl acetate, heptane, hexane, cyclohexane, toluene, xylene, methylene chloride, 1,1-dichloroethane, 1,1,2-trichloroethane, acetone, methyl ethyl ketone, methyl isobutyl ketone, acetonitrile, dimethylformamide, dimethylacetamide, dimethylsulphoxide, chlorobenzene or mixtures thereof.

Alternatively, in the case in which acetic acid is not used, the reaction solvent consists of one of the above-mentioned organic solvents, or a mixture thereof, to which there is added an acid selected from oxalic acid, citric acid, para toluene sulphonic acid, formic acid, sulphuric acid, perchloric acid, hydrochloric acid, phosphoric acid, nitric acid, hydrobromic acid, fumaric acid, maleic acid, xinafoic acid (1-hydroxy-2-naphthoic acid), benzoic acid and substitution derivatives thereof on the aromatic ring, or bisulfites of alkali metals or alkaline-earth metals.

The protic acids mentioned can be used in anhydrous form or in any known hydrated forms (for example, in the case of oxalic and para toluene sulphonic acids, commonly available commercially in the form of the monohydrates thereof), or in the form of aqueous solutions (for example in the case of hydrochloric acid, commonly available commercially as an aqueous solution at the maximum stable concentration, of about 37% by weight, or at a concentration equal to about 18% by weight, or nitric acid).

Preferred solvents for the reaction are pure acetic acid (known in chemistry as "glacial") and mixtures of one or more of the above-mentioned organic solvents and an acid selected from acetic acid, citric acid or potassium bisulfite monohydrate.

The oxidation reaction can be carried out at a temperature of between 30 and 50° C., and preferably of between 30 and 40° C., for a time of between 2 and 24 hours, preferably of between 6 and 20 hours.

The crude drospirenone obtained with the present process is purifiable with techniques known to persons skilled in the art and described in publications and patents; for example, purification can be achieved by crystallization from isopropyl acetate, as described in patent EP 1828222 B1. The inventors have found that the yields of drospirenone the process vary between about 60 and 85%.

The invention will be further illustrated by the following examples, which are provided by way of an illustrative and non-limiting example of the present invention. The reagents used in the examples are commonly available commercially and are used without the need for preventive purifications. All concentrations are expressed as weight percentages unless otherwise specified.

EXAMPLE 1

Into a 100 ml flask is loaded 1 g of 17α-(3-hydroxypropyl)-6β,7β;15β,16β-dimethylene -5β-androstane-3β,5,17β-triol (II) into 3 ml of glacial acetic acid.

200 mg of ferric nitrate nonahydrate, 78 mg of TEMPO and 29 mg of sodium chloride are added.

The reagent mixture is stirred at 35° C. for 16 hours in an atmosphere of pure oxygen. The progress of the reaction is monitored by TLC from which there is found the disappearance of the starting product (II) and the formation of drospirenone (I) (by comparison against samples of the pure compounds obtained by methods known in the field).

At the end of the reaction the reaction mixture is poured into 12 ml of water, it is extracted with ethyl acetate thus obtaining, after evaporation of the solvent, 1.05 g of residue.

By means of HPLC analysis (European Ph method) the previous TLC findings are confirmed: intermediate (II) absent, drospirenone (I) present. The crude product, crystallized from isopropyl acetate as per a method known in literature, provides a product of pharmaceutical quality.

EXAMPLE 2

In a 100 ml flask are loaded 5 g of 17α-(3-hydroxypropyl)-6β,7β;15β,16β-dimethylene -5β-androstane-3β,5,17β-triol (II) into 30 ml of methylene chloride.

1 g of ferric nitrate nonahydrate, 400 mg of TEMPO and 150 mg of sodium chloride and 250 mg of citric acid are added.

The reagent mixture is stirred at 35° C. for 20 hours in an atmosphere of pure oxygen. The progress of the reaction is monitored by TLC from which there is found the disappearance of the starting product (II) and the formation of drospirenone (I) (by comparison against samples of the pure compounds obtained by methods known in the field).

At the end of the reaction the reaction mixture is poured into 30 ml of water, the phases are separated and the organic phase is washed with basic solution (NaHCO$_3$).

After evaporation of the solvent 5.2 g of raw product are obtained.

By means of HPLC analysis (European Ph method) the previous TLC findings are confirmed: intermediate (II) absent, drospirenone (I) present. The crude product, crystallized from isopropyl acetate as per a method known in literature, provides a product of pharmaceutical quality.

EXAMPLE 3

Into a 2 litre flask are loaded 23.3 g of ferric nitrate nonahydrate, 12.2 g of TEMPO, 4.5 g of sodium chloride, 750 ml of isopropyl acetate, 7.5 g of citric acid and 150 g of 17α-(3-hydroxypropyl)-6β,7β;15β,16β-dimethylene-5β-androstane -3β,5,17β-triol (II).

The mixture is stirred at 35° C. in an atmosphere of pure oxygen. The progress of the reaction is monitored after 18 hours by TLC from which there is found the disappearance of the starting product (II) and the formation of drospirenone (I) as main stain (comparison against an authentic sample).

The reaction mixture is washed with 250 ml of basic aqueous solution (NaHCO$_3$) and then with 250 ml of water.

The solvent is eliminated under reduced pressure thus obtaining 170 g of residue.

After crystallization with isopropyl acetate and dessication of the filtrate solid, there are obtained 104 g of drospirenone (I) of pharmaceutical quality.

EXAMPLE 4

Into a 100 ml flask are loaded 5 g of 17α-(3-hydroxypropyl)-6β,7β;15β,16β-dimethylene -5β-androstane-3β,5,17β-triol (II) in 25 ml of butyl acetate.

775 mg of ferric nitrate nonahydrate, 400 mg of TEMPO, 150 mg of sodium chloride and 250 mg of citric acid are added.

The reagent mixture is stirred at 35° C. for 20 hours in an atmosphere of pure oxygen. The progress of the reaction is monitored by TLC from which there is found the disappearance of the starting product (II) and the formation of drospirenone (I) (by comparison against samples of the pure compounds obtained by methods known in the field).

At the end of the reaction the reaction mixture is poured into 30 ml of water, the phases are separated and the organic phase is washed with basic solution (NaHCO$_3$).

After evaporation of the solvent 5.12 g of raw product are obtained.

By means of HPLC analysis (European Ph method) the previous TLC findings are confirmed: intermediate (II) absent, drospirenone (I) present. The crude product, crystallized from isopropyl acetate as per a method known in literature, provides a product of pharmaceutical quality.

EXAMPLE 5

Into a 100 ml flask are loaded 5 g of 17α-(3-hydroxypropyl)-6β,7β;15β,16β-dimethylene -5β-androstane-3β,5,17β-triol (II) into 25 ml of chlorobenzene-isopropyl acetate 80/20.

There are added 770 g of ferric nitrate nonahydrate, 400 mg of TEMPO, 150 mg of sodium chloride and 250 mg of citric acid.

The reagent mixture is stirred while bringing the temperature from the initial value of 30° C. to 45° C. over a period of 20 hours in pure oxygen atmosphere.

The progress of the reaction is monitored by TLC from which there is found the disappearance of the starting product (II) and the formation of drospirenone (I) (by comparison against samples of the pure compounds obtained by methods known in the field).

At the end of the reaction the reaction mixture is poured into 30 ml of water, the phases are separated and the organic phase is washed with basic solution (NaHCO$_3$) and then with water.

After evaporation of the solvent 5.05 g of raw product are obtained.

By means of HPLC analysis (European Ph method) the previous TLC findings are confirmed: intermediate (II) absent, drospirenone (I) present. The crude product, crystallized from isopropyl acetate as per a method known in literature, provides a product of pharmaceutical quality.

The invention claimed is:

1. A process for the preparation of drospirenone of the formula (I):

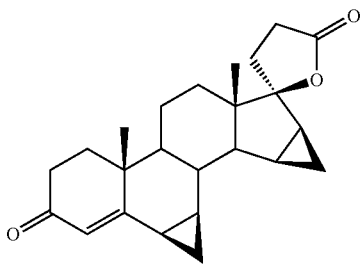

comprising the step of:
reacting 17α-(3-hydroxypropyl)-6β,7β;15β,16β-dimethylene -5β-androstane-3β,5,17β-triol of the formula (II):

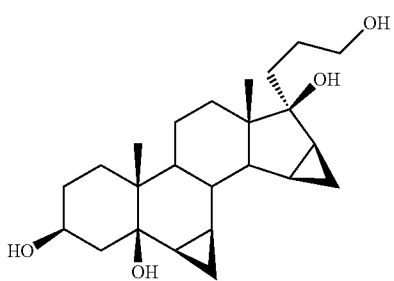

with oxygen, at a temperature in the range of 30° C. to 50° C., in the presence of acetic acid, or a mixture of an acid and at least one organic solvent, and a catalytic system consisting of ferric nitrate nonahydrate, sodium chloride and 2,2,6,6-tetramethylpiperidine-1-oxyl radical, or a derivative thereof, selected from the group consisting of 4-hydroxy-2,2,6,6-tetramethylpiperidine-1-oxyl radical, 4-methoxy-2,2,6,6 -tetramethylpiperidine-1-oxyl radical, 4-(benzoyloxy)-2,2,6,6-tetramethylpiperidine-1-oxyl radical, 4-acetamido-2,2,6,6-tetramethylpiperidine-1-oxyl radical and 4-amino-2,2,6,6-tetramethylpiperidine-1-oxyl radical;
wherein each of the catalytic system components is present in a molar ratio of 15% to 25% in moles with respect to 17α-(3-hydroxypropyl)-6β,7β;15β,16β-dimethylene -5β-androstane-3β,5,17β-triol of the formula (II).

2. The process according to claim 1, wherein the oxygen is pure oxygen, air or a mixture of one or more inert gases and oxygen.

3. The process according to claim 1, wherein the acid is selected from the group consisting of acetic acid, oxalic acid, citric acid, para-toluenesulfonic acid, formic acid, sulfuric acid, perchloric acid, hydrochloric acid, phosphoric acid, nitric acid, hydrobromic acid, fumaric acid, maleic acid, xinafoic acid, benzoic acid, an alkali metal bisulfite and an alkaline-earth metal bisulfite.

4. The process according to claim 1, wherein the acid is aqueous.

5. The process according to claim 1, wherein the organic solvent is selected from the group consisting of diethyl ether, diisopropyl ether, methyl t-butyl ether, tetrahydrofuran, methyltetrahydrofuran, ethyl acetate, isopropyl acetate, butyl acetate, heptane, hexane, cyclohexane, toluene, xylene, methylene chloride, 1,1-dichloroethane, 1,1,2-trichloroethane, acetone, methyl ethyl ketone, methyl isobutyl ketone, acetonitrile, dimethylformamide, dimethylacetamide, dimethylsulfoxide, chlorobenzene and mixtures thereof.

* * * * *